United States Patent
Powell et al.

(10) Patent No.: US 6,224,847 B1
(45) Date of Patent: *May 1, 2001

(54) PROCESS FOR THE EXTRACTION OF A COMPOUND BY A FLUOROCARBON COMPOUND

(75) Inventors: Richard Llewellyn Powell, Tarporley; Timothy James Noakes, Near Mold; Peter Frederick Wilde, Thirsk, all of (GB)

(73) Assignee: Imperial Chemical Industries PLC, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/716,269

(22) PCT Filed: Mar. 15, 1995

(86) PCT No.: PCT/GB95/00554

§ 371 Date: Jan. 31, 1997

§ 102(e) Date: Jan. 31, 1997

(87) PCT Pub. No.: WO95/26794

PCT Pub. Date: Oct. 12, 1995

(30) Foreign Application Priority Data

Mar. 31, 1994 (GB) .................................................. 9406423

(51) Int. Cl.$^7$ ................................ A23L 1/00; C11B 1/00; A24B 15/26; B01D 11/00

(52) U.S. Cl. ........................ 423/658.5; 426/428; 426/429; 426/430; 554/8; 554/9; 554/13; 554/14; 131/298

(58) Field of Search .................... 423/658.5; 426/429, 426/430, 428; 554/8, 9, 13, 14; 131/298; 514/759, 783; 424/195.1; 510/408, 415

(56) References Cited

U.S. PATENT DOCUMENTS

| | | | |
|---|---|---|---|
| 3,612,066 | * 10/1971 | Jones et al. | 131/298 |
| 3,769,033 | 10/1973 | Panzer et al. | 426/428 |
| 3,928,579 | 12/1975 | McShane . | |
| 4,059,604 | 11/1977 | Kresse . | |
| 5,018,540 | * 5/1991 | Grubbs et al. | 423/658.5 |
| 5,092,983 | * 3/1992 | Eppig et al. | 208/323 |
| 5,281,732 | * 1/1994 | Franke | 554/16 |
| 5,405,633 | * 4/1995 | Heidlas et al. | 426/442 |
| 5,512,285 | * 4/1996 | Wilde | 424/195.1 |
| 5,516,923 | * 5/1996 | Herbert et al. | 554/12 |
| 5,824,225 | * 10/1998 | Powell et al. | 210/656 |

FOREIGN PATENT DOCUMENTS

| | | |
|---|---|---|
| 0 616 821 | 9/1994 | (EP) . |
| 1 419 958 | 12/1975 | (GB) . |
| 2 225 205 | 5/1990 | (GB) . |

* cited by examiner

Primary Examiner—Steven Bos
(74) Attorney, Agent, or Firm—Cook, Alex, McFarron, Manzo, Cummings & Mehler, Ltd.

(57) ABSTRACT

A process for extracting a compound or composition of matter from a raw material containing that compound or composition as a constituent part is disclosed. The process comprises the steps of (1) contacting a sample of the raw material with an extraction solvent comprising 1,1,1,2-tetrafluoroethane and a co-solvent selected from an alkane and a hydrocarbon ether, (2) forming a solvent liquor comprising the extraction solvent and an extract from the raw material, and (3) separating the solvent liquor containing the extract from the raw material.

28 Claims, No Drawings

PROCESS FOR THE EXTRACTION OF A COMPOUND BY A FLUOROCARBON COMPOUND

The present invention relates to a solvent extraction process in which a raw material containing a particular compound or composition is treated with an extraction solvent so as to remove at least a proportion of that compound or composition from the raw material.

Processes for extracting a desired compound or composition from a raw or bulk material which contains that compound or composition as a constituent part using a suitable extraction solvent are known in the art. In these known processes, the raw material is contacted with the extraction solvent, often under vigorous mixing conditions so as to facilitate the dissolution of the desired compound or composition into the extraction solvent, and the resulting solvent liquor containing the desired compound or composition is then separated from the raw material for subsequent processing, e.g. distillation to remove the extraction solvent. Multiple extractions may suitably be carried out on the same raw material sample so as to maximise the amount of the desired compound or composition which is extracted from that sample. Typical examples of extraction solvents which have been used in the prior art extraction processes include hexane, methyl acetate, ethyl acetate, acetone and methanol.

Although solvent extraction processes are used on a commercial scale, the extraction solvents which are currently used in these processes are not wholly satisfactory. Thus, when solvents such as hexane are used to extract flavoured or aromatic oils, such as are used in the food and cosmetic industries, from plant matter containing those oils, unwanted materials contained in the plant, e.g. high molecular weight waxes, tend to be eluted along with the desired oil. This problem necessitates subjecting the resultant hexane liquor to further processing in which the unwanted waxes are removed by extraction, e.g. using ethanol. Furthermore, the extraction solvents which are currently in use have fairly high boiling points, and the elevated temperatures which are employed in the distillation process to remove these high boiling solvents from the extracted material can cause problems. For example, the flavoured or aromatic oils contained in certain plants are complex substances containing a large number of individual compounds some of which are relatively volatile or relatively thermally unstable. Consequently, high distillation temperatures can tend to result in a loss of product either through co-evaporation of the more volatile compounds with the extraction solvent or thermal degradation of the more thermally unstable compounds.

The present invention provides a new solvent extraction process which can be used to extract a wide variety of compounds or compositions from raw or bulk materials of which they form a constituent part. In one particular embodiment, the present invention provides a solvent extraction process which is capable of extracting the flavoured or aromatic oils contained in certain plant materials without eluting the high molecular weight waxes they contain.

According to the present invention there is provided a process for extracting a compound or composition of matter from a raw material containing that compound or composition as a constituent part, which process comprises the steps of (1) contacting a sample of the raw material with an extraction solvent comprising a $C_{1-4}$ (hydro)fluorocarbon and a co-solvent, and (2) separating the solvent liquor thus obtained containing the extract from the raw material.

In one particular embodiment, the extraction process of the present invention can be used to extract a natural product, such as a flavoured or aromatic oil, from a plant material containing that product.

Accordingly, the present invention provides a process for extracting a natural product from a plant material containing that product as a constituent part, which process comprises the steps of (1) contacting a sample of the plant material with an extraction solvent comprising a $C_{1-4}$ (hydro)fluorocarbon and a co-solvent, and (2) separating the solvent liquor thus obtained containing the extract from the plant material.

When used in this specification, the expression "plant material" not only includes materials which are essentially unprocessed and as such are clearly recognisable as being of plant origin, for example bark, leaves, flowers and seeds, but also materials, which although originating from plants, have been subjected to various processes and as such have a form which is somewhat different than the plants from which they originated, for example ground cumin and ground ginger.

In a further embodiment, the extraction process of the present invention can be used to extract a biologically active compound, such as a pesticide or a pharmaceutically active substance, or a precursor to such a compound from a raw material containing that compound or precursor, such as a plant material, a cell culture or a fermentation broth.

Accordingly, the present invention provides a process for extracting a composition comprising a biologically active compound or a precursor thereof from a raw material containing that composition as a constituent part, which process comprises the steps of (1) contacting a sample of the raw material with an extraction solvent comprising a $C_{1-4}$ (hydro)fluorocarbon, and (2) separating the solvent liquor thus obtained containing the extract from the raw material.

Suitable pesticides which may be extracted using the extraction process of the present invention include insecticides such as the pyrethroids.

Suitable pharmaceutically active substances which may be extracted using the extraction process of the present invention include the penicillins, the alkaloids, paclitaxel, monensin and cytochalasin. Precursors to these compounds may also be extracted using the extraction process of the present invention. In one particular application for the extraction process of the present invention, paclitaxel, which is an important anti-cancer drug, and/or taxane, which is a precursor to paclitaxel, can be extracted from yew tree products, such as the bark or needles harvested from these trees. When the extraction process is used to extract a biologically active compound or precursor thereof, the extraction solvent which is used will preferably comprise a co-solvent in addition to the $C_{1-4}$ (hydro)fluorocarbon.

According to a further aspect of the present invention, there is provided a composition comprising a pharmaceutically active substance obtained from a raw material product using the extraction process of the present invention.

According to a still further aspect of the present invention, there is provided a composition comprising a pharmaceutically active substance obtained from a raw material product using the extraction process of the present invention for use in medicine.

The present invention also provides a process for extracting a composition comprising one or more polar group containing compounds from a raw material containing that composition as a constituent part, such as a plant material, which process comprises the steps of (1) contacting a sample of the raw material with an extraction solvent comprising a $C_{1-4}$ (hydro)fluorocarbon and a co-solvent, and (2) separating the solvent liquor thus obtained containing the extract from the raw material.

The extraction solvent which is used in the process of the present invention comprises a $C_{1-4}$ (hydro)fluorocarbon (i.e. a (hydro)fluorocarbon having from 1 to 4 carbon atoms). Mixtures of two or more (hydro)fluorocarbons may be used if desired. By the term (hydro)fluorocarbon we mean a compound selected from the group consisting of the hydrofluorocarbons and the perfluorocarbons.

Although extraction solvents comprising a perfluorocarbon such as perfluoropropane may be usefully employed in the process of the present invention, the preferred extraction solvents will comprise one or more hydrofluorocarbons. Hydrofluorocarbons having from 1 to 3 carbon atoms, especially the hydrofluoromethanes, hydrofluoroethanes and hydrofluoropropanes, are more preferred, and of these the hydrofluorocarbons having 2 carbon atoms, especially the hydrofluoroethanes, are particularly preferred. Examples of hydrofluoromethanes, hydrofluoroethanes and hydrofluoropropanes which may be useful in the extraction process of the present invention include, inter alia, trifluoromethane, fluoromethane, difluoromethane, pentafluoroethane, 1,1,1-trifluoroethane, 1,1,2,2-tetrafluoroethane, 1,1,1,2-tetrafluoroethane, 1,1,1,2,3,3-hexafluoropropane, 1,1,1,2,2,3-hexafluoropropane and 1,1,1,3,3,3-hexafluoropropane.

The preferred (hydro)fluorocarbons have a boiling point of 15° C. or below, for example in the range of from −85 to 15° C., preferably 0° C. or below, for example in the range of from −85 to 0° C., and more preferably −10° C. or below, for example in the range of from −70 to −10° C. An especially preferred hydrofluorocarbon is 1,1,1,2-tetrafluoroethane (R-134a).

The co-solvent which may be used in combination with the $C_{1-4}$ (hydro)fluorocarbon will typically have a boiling point of 60° C. or below, for example in the range of from −85 to 60° C. The preferred co-solvents have a boiling point of 20° C. or below, for example in the range of from −85 to 20° C. preferably 10° C. or below, for example in the range of from −70 to 10° C., and more preferably 0° C. or below, for example in the range of from −60 to 0° C. Mixtures of two or more co-solvents may be used if desired. Suitable co-solvents may be selected from the $C_{2-6}$, particularly the $C_{2-4}$ hydrocarbon compounds which may be aliphatic or alicyclic. Preferred hydrocarbons are the alkanes and cycloalkanes, with alkanes such as ethane, n-propane, i-propane, n-butane and i-butane being especially preferred. Other compounds which may be usefully employed as co-solvents in the extraction process of the present invention include the hydrocarbon ethers, particularly the dialkyl ethers, such as dimethyl ether, methyl ethyl ether and diethyl ether. Dimethyl ether and butane are particularly preferred co-solvents and of these dimethyl ether is especially preferred.

The extraction solvent preferably comprises from 50.0 to 99.5% by weight, more preferably from 70.0 to 99.0% by weight, and particularly preferably from 80.0 to 98.0% by weight of the one or more $C_{1-4}$ (hydro)fluorocarbons and from 50.0 to 0.5% by weight, more preferably from 30.0 to 1.0% by weight, and particularly preferably from 20.0 to 2.0% by weight of the one or more co-solvents. If the co-solvent is a flammable material, which will be the case with the hydrocarbon and hydrocarbon ethers identified above, then the extraction solvent will preferably comprise sufficient of the (hydro)fluorocarbon to render it non-flammable overall. Where the extraction solvent is a blend of one or more (hydro)fluorocarbons and one or more co-solvents, the resulting blend may be zeotropic, but is preferably azeotropic or azeotrope-like. Azeotropic and azeotrope-like blends are preferred, since they behave essentially as a single substance.

The extraction solvent which is used in the process of the present invention may be in liquid, gaseous or vaporous form, but is preferably in liquid form.

The raw material which is subjected to the present extraction process may be a liquid, e.g. a solution, suspension or emulsion, or a solid. If the raw material is a solid, then the efficiency of the extraction process may be significantly improved by reducing the solid to a finely divided form, such as a powder.

The contacting of the extraction solvent with the raw material to be processed may be carried out under vigorous mixing conditions so as to facilitate the dissolution of the material to be extracted into the extraction solvent. The vigorous mixing may be achieved by mechanically shaking the extraction vessel containing the raw material/extraction solvent mixture or by stirring that mixture.

After the extraction process of the present invention has been completed, the solvent liquor containing the extract can be distilled to remove the extraction solvent from the extract. The resulting extract may then be used as it is or, alternatively, it may be subjected to one or more further processes, for example to purify the extract or to isolate a given compound or compounds contained in the extract.

In the preferred extraction process of the present invention, the extraction solvent which is used comprises a (hydro)fluorocarbon which has a relatively low boiling point compared to the extraction solvents used hitherto and, moreover, where a co-solvent is used this will likewise generally have a relatively low boiling point. In consequence, once the extraction process of the present invention has been completed to yield a solvent liquor containing the extract, the removal of the extraction solvent from the liquor tends to be relatively facile allowing the distillation to be carried out at relatively low temperatures, e.g. room temperature and below. This in turn reduces the risk of loosing desired product either through co-evaporation of the more volatile compounds with the extraction solvent or thermal degradation of the more thermally unstable compounds.

The extraction process of the present invention may be operated continuously with the same extraction solvent being used repeatedly. A suitable installation for carrying out a continuous extraction process typically comprises an extraction vessel, a distillation unit, a compressor, a condenser and a suitable arrangement of connecting pipe work. The extraction solvent is first charged to the extraction vessel where it is contacted with the raw material to be processed, possibly under vigorous mixing conditions so as to facilitate the dissolution of the compound or composition to be extracted into the extraction solvent. The resulting solvent liquor containing the extract is then separated from the raw material, e.g. by allowing the liquor to drain through a filter arranged at the bottom of the extraction vessel, and passed to the distillation unit where the extraction solvent is removed by evaporation to leave the extract. The vapour generated in the distillation unit is compressed, e.g. using a diaphragm compressor, and is then delivered to a condenser which returns the extraction solvent to liquid form for recharging to the extraction vessel. With a continuous extraction process of this kind, it is possible to maximise the amount of the extract obtained without subjecting the same raw material sample to a succession of individual extractions. Once the raw material sample is exhausted, it is then removed from the extraction vessel and replaced with a fresh raw material sample.

The present invention is now illustrated but not limited by the following examples.

General Procedure

The extraction apparatus comprised a glass bottle having an aerosol valve fitting attached to its mouth. The aerosol valve fitting was equipped with a dip pipe which extended to the bottom of the glass bottle. The dip pipe was itself equipped with a glass wool filter at its lower end so as to prevent solids from rising up its length during transfer of the solvent liquor to the evaporation/collection system described later. The raw material to be processed was placed in the glass bottle, the aerosol valve fitting with its dip pipe was fixed in position and the extraction solvent was then charged to the glass bottle via the aerosol valve and dip pipe. After the required amount of extraction solvent had been charged to the glass bottle. the extraction apparatus was clamped to a mechanical shaker to intimately mix the extraction solvent with the raw material. The extraction apparatus was removed from the mechanical shaker after a set period of time.

An evaporation/collection system comprising (a) an evaporation chamber for vaporising the extraction solvent, (b) an inlet pipe for charging the solvent liquor containing the extract to the evaporation chamber, (c) an outlet pipe for discharging the vaporised extraction solvent from the evaporation chamber, and (d) a small collecting duct situated at the bottom of the evaporation chamber for containing the extract was then connected to the extraction apparatus by means of a length of transfer tubing extending from the inlet pipe of the evaporation/collection system to the aerosol valve fitting of the extraction apparatus. The solvent liquor containing the extract was then transferred from the extraction apparatus to the evaporation/collection system by depressing the aerosol valve which forced the solvent liquor up the dip pipe, into the transfer tubing and then into the evaporation chamber via the inlet pipe. The transfer was effected gradually by a series of short depressions of the aerosol valve and the extraction solvent was allowed to flash off between each depression. The evaporation of the extraction solvent was aided by immersing the lower half of the evaporation chamber in an ambient temperature water bath. The extract was collected in the collecting duct.

EXAMPLES 1 AND 2

In these examples, the general procedure described above was used to extract and collect the oil contained in a sample of ground cumin. The extraction solvent used was a mixed solvent system comprising 1,1,1,2-tetrafluoroethane (R-134a) and dimethyl ether (DME). In Example 1, the weight ratio of R-134a:DME in the extraction solvent was about 95:5. In Example 2, the weight ratio of R-134a:DME in the extraction solvent was about 90:10.

About 10 g of ground cumin and about 50 g of the R-134a/DME extraction solvent were used in the extraction to give a cumin:solvent weight ratio of about 1:5. The DME was charged first followed by the R-134a so as to give a mixed extraction solvent having the required proportions of R-134a and DME. The extraction apparatus was removed from the mechanical shaker after approximately 1 hour.

As a control experiment, the extraction of oil from ground cumin was investigated using pure R-134a. The above described general procedure was used to carry out the extraction and to isolate the desired oil. About 10 g of ground cumin and about 50 g of R-134a were used in this control experiment. The extraction apparatus was removed from the mechanical shaker after approximately 1 hour.

The cumin oil extracts obtained in the two examples and in the control experiment were weighed and the percentage of oil extracted determined. The results are shown in Table 1 together with the exact weights of cumin, R-134a and DME used in the extraction and the calculated weight ratios. Each of the cumin oil extracts were also examined by gas liquid chromatography (GLC).

TABLE 1

|  | Control | Example 1 | Example 2 |
| --- | --- | --- | --- |
| Weight of DME (g) | 0 | 2.42 | 5.09 |
| Weight of R-134a (g) | 50.40 | 48.98 | 46.12 |
| Total weight of solvent (g) | 50.40 | 51.40 | 51.21 |
| R-134a: DME weight ratio | 100:0 | 95.3:4.7 | 90.1:9.9 |
| Weight of ground cumin (g) | 9.25 | 10.0 | 10.0 |
| Cumin: solvent weight ratio | 1:5.45 | 1:5.14 | 1:5.12 |
| Weight of cumin oil extracted (g) | 0.15 | 0.21 | 0.26 |
| Percentage of oil extracted | 1.62 | 2.10 | 2.60 |

EXAMPLES 3 TO 6

In these examples, the general procedure described above was used to extract and collect the oil contained in a further sample of ground cumin. In Examples 3 and 4, the extraction solvent used was a mixed solvent system comprising R-134a and DME. In Example 3, the weight ratio of R-134a:DME in the extraction solvent was about 95:5. In Example 4, the weight ratio of R-134a:DME in the extraction solvent was about 90:10. In Examples 5 and 6, the extraction solvent used was a mixed solvent system comprising R-134a and butane. In Example 5, the weight ratio of R-134a:butane in the extraction solvent was about 95:5. In Example 6, the weight ratio of R-134a:butane in the extraction solvent was about 90:10.

About 10 g of ground cumin and about 50 g of the R-134a/DME or R-134a/butane extraction solvent were used in the extraction to give a cumin:solvent weight ratio of about 1:5. The DME or butane was charged first followed by the R-134a so as to give a mixed extraction solvent having the required proportions of R-134a and DME or R-134a and butane. The extraction apparatus was removed from the mechanical shaker after approximately 1 hour.

As a control experiment, the extraction of oil from the ground cumin was investigated using pure R-134a. The above described general procedure was used to carry out the extraction and to isolate the desired oil. About 10 g of ground cumin and about 50 g of R-134a were used in this control experiment. The extraction apparatus was removed from the mechanical shaker after approximately 1 hour.

The cumin oil extracts obtained in the four examples and in the control experiment were weighed and the percentage of oil extracted determined. The results are shown in Tables 2 and 3 together with the exact weights of cumin, R-134a, DME and butane used in the extraction and the calculated weight ratios. Each of the cumin oil extracts were also examined by gas liquid chromatography (GLC).

TABLE 2

|  | Control | Example 3 | Example 4 |
|---|---|---|---|
| Weight of DME (g) | 0 | 2.50 | 4.49 |
| Weight of R-134a (g) | 51.21 | 48.69 | 46.11 |
| Total weight of solvent (g) | 51.21 | 51.19 | 50.60 |
| R-134a: DME weight ratio | 100:0 | 95.1:4.9 | 91.1:8.9 |
| Weight of ground cumin (g) | 10.0 | 10.0 | 10.0 |
| Cumin: solvent weight ratio | 1:5.12 | 1:5.12 | 1:5.06 |
| Weight of cumin oil extracted (g) | 0.16 | 0.25 | 0.43 |
| Percentage of oil extracted | 1.60 | 2.50 | 4.30 |

TABLE 3

|  | Control | Example 5 | Example 6 |
|---|---|---|---|
| Weight of butane (g) | 0 | 2.60 | 5.18 |
| Weight of R-134a (g) | 51.21 | 46.57 | 44.02 |
| Total weight of solvent (g) | 51.21 | 49.17 | 49.20 |
| R-134a: butane weight ratio | 100:0 | 94.7:5.3 | 89.5:10.5 |
| Weight of ground cumin (g) | 10.0 | 10.0 | 10.0 |
| Cumin: solvent weight ratio | 1:5.12 | 1:4.92 | 1:4.92 |
| Weight of cumin oil extracted (g) | 0.16 | 0.19 | 0.30 |
| Percentage of oil extracted | 1.60 | 1.90 | 3.0 |

By comparing the results of Examples 1 to 6 with those of the control experiments, it can be seen that the addition of butane and particularly DME to the R-134a considerably improves the effectiveness of the extraction process with much better yields of the cumin oil extract being obtained. Moreover, the yield of the cumin oil obtained in the extraction increases with increasing concentration of butane and DME in the extraction solvent. The fragrance of the cumin oil also changes with the use of a mixed extraction solvent. Compared to the oil obtained using pure R-134a, the oils obtained using the mixed extraction solvents have a richer and more complex fragrance. This difference in fragrance is reflected in the more complex GLC traces (i.e. more peaks at higher retention times) which are obtained for oils extracted using mixed extraction solvents.

EXAMPLES 7 TO 9

In these examples, the general procedure described above was used to examine the extraction of paclitaxel contained in yew tree needles harvested from the European Yew. Three different extractions were carried out each using a different extraction solvent.

In Example 7, pure R-134a was used as the extraction solvent. 10 g of ground, air-dried yew needles and 50 g of R-134a were used in the extraction to give a yew needle:solvent weight ratio of 1:5. Mechanical shaking of the extraction solvent/yew needle mixture was continued for approximately 5 minutes. At the end of the experiment, i.e. following removal of the R-134a in accordance with the above described general procedure, 0.012 g of an oily product was obtained. This product was analysed by high performance liquid chromatography (HPLC) and was shown to contain paclitaxel.

In Example 8, a mixed solvent system comprising 90 parts by weight of R-134a and 10 parts by weight of DME was used as the extraction solvent. A 10 g sample of ground, air-dried yew needles was subjected to three successive extractions each of which was carried out in accordance with the above described general procedure.

In the first extraction, the yew needles were treated with 50 g of the R-134a/DME extraction solvent. Mechanical shaking of the extraction solvent/yew needle mixture was continued for approximately 5 minutes. At the end of this first extraction, 0.025 g of a wax was collected following evaporation of the extraction solvent.

A further 46.8 g of the R-134a/DME extraction solvent was then charged to the glass aerosol bottle and the second extraction of the ground yew needles was carried out. In this second extraction, mechanical shaking of the extraction solvent/yew needle mixture was continued for approximately 5 minutes. At the end of this second extraction, a further 0.035 g of material in the form of a wax was collected following evaporation of the extraction solvent.

Finally, a further 50 g of the R-134a/DME extraction solvent was charged to the glass aerosol bottle and the third and final extraction of the ground yew needles was initiated. In this third extraction, mechanical shaking of the extraction solvent/yew needle mixture was continued for approximately 90 minutes. At the end of this third extraction, a further 0.026 g of material in the form of an oily wax was collected.

The cumulative weight of the extracts obtained in the three extractions was 0.086 g giving a percentage yield of 0.86%. Each of these extracts was analysed by high performance liquid chromatography (HPLC) and was shown to contain paclitaxel.

In Example 9, a mixed solvent system comprising 90 parts by weight of R-134a and 10 parts by weight of butane was used as the extraction solvent. A 10 g sample of ground, air-dried yew needles was subjected to two extractions each of which was carried out in accordance with the above described general procedure.

In the first extraction, the yew needles were treated with 50 g of the R-134a/butane extraction solvent. Mechanical shaking of the extraction solvent/yew needle mixture was continued for approximately 5 minutes. At the end of this first extraction, 0.021 g of an oily wax was collected following removal of the extraction solvent.

A further 50.0 g of the R-134a/butane extraction solvent was then charged to the glass aerosol bottle and the second extraction of the ground yew needles was carried out. In this second extraction, mechanical shaking of the extraction solvent/yew needle mixture was continued for approximately 5 minutes. At the end of this second extraction, a further 0.018 g of material in the form of an oily wax was collected following removal of the extraction solvent.

The cumulative weight of the extracts obtained in the two extractions was 0.039 g giving a percentage yield of 0.39%. Each of these extracts was analysed by high performance liquid chromatography (HPLC) and was shown to contain paclitaxel.

EXAMPLE 10

In this example, the general procedure described above was used to examine the extraction of monensin, particularly monensin A, from an aqueous solution containing, inter alia, monensin A and monensin B using R-134a as the extraction solvent.

20 mls of the aqueous solution containing the monensin compounds and 50 g of R-134a were used in this extraction. Mechanical shaking of the R-134a/monensin solution mixture was continued for approximately 30 minutes with an emulsion being formed. The emulsion was left to stand for about 1 hour and the glass aerosol bottle containing the emulsion was then immersed in a beaker of warm (about 40° C.) water for 1 hour so as to encourage the break-up of the emulsion and the separation of the R-134a solvent liquor. After ½ hour in the warm water, the R-134a solvent liquor separated out forming the bottom layer with the extracted aqueous solution forming the top layer.

A proportion of the R-134a solvent liquor was then transferred to the evaporation/collection system and the extract contained in this liquor isolated in accordance with the above described general procedure. A damp oily residue was collected which was examined using thin layer chromatography (TLC) as described below in order to assess whether the monensin A had been successfully extracted by the R-134a.

The damp oily residue contained in the collecting duct was taken up into a small volume of dichloromethane and a sample of the resulting dichloromethane solution was spotted onto a TLC plate. A sample of commercially available monensin A, similarly dissolved in dichloromethane, was then spotted onto the same TLC plate so as to run the two samples in parallel for comparison. The TLC plate was run using a 50:50 mixture by volume of dichloromethane and ethyl acetate as the solvent and was then developed so that the monensin A could be visually observed on the TLC plate. The TLC trace of the extract (i.e. the damp oily residue) and that of the commercially available monensin A each included a spot about ¼ of the way up the TLC plate clearly indicating that the R-134a had successfully extracted at least a proportion of the monensin A contained in the crude aqueous solution.

The aqueous solution remaining after the extraction was also analysed by TLC in order to confirm that the monensin A was present in the oily residue extracted by the R-134a and not the aqueous solution contaminating this residue which was carried over with the R-134a solvent liquor during the transfer operation. A small sample of the aqueous layer remaining after the extraction was extracted with dichloromethane and the resulting dichloromethane solution analysed by TLC as before. No monensin A was detected thus confirming that the monensin A was extracted by the R-134a.

EXAMPLE 11

In this example, the general procedure described above was used to examine the extraction of cytochalasin D from an aqueous solution containing this compound as a constituent part using R-134a as the extraction solvent.

50 g of the aqueous solution containing the cytochalasin D and 30 g of R-134a were used in this extraction. Mechanical shaking of the R-134a/cytochalasin solution mixture was continued for approximately 5 minutes with an emulsion being formed. The emulsion was left to stand for about 2 hours after which the R-134a solvent liquor separated out forming the lower layer with the extracted aqueous solution forming the upper layer.

A proportion of the R-134a solvent liquor was then transferred to the evaporation/collection system and the extract contained in this liquor isolated in accordance with the above described general procedure. Some water droplets were also transferred during this operation so that the final extract was slightly damp. This extract was then examined using thin layer chromatography (TLC) as described below in order to assess whether the cytochalasin D had been successfully extracted by the R-134a.

The extract contained in the collecting duct was taken up into a small volume of ethyl acetate and a sample of the resulting ethyl acetate solution was spotted onto a TLC plate. A sample of pure cytochalasin D in pyridine was then spotted onto the same TLC plate so as to run the two samples in parallel for comparison. The TLC plate was run using ethyl acetate as the solvent and was then examined under a UV lamp. The TLC trace of the extract and that of the pure cytochalasin D sample each included a spot (visible under UV) about ½ of the way up the TLC plate clearly indicating that the R-134a had successfully extracted at least a proportion of the cytochalasin D contained in the crude aqueous solution.

The aqueous solution remaining after the extraction was also analysed by TLC in order to confirm that the cytochalasin D was present in the material extracted by the R-134a and not the aqueous solution contaminating this material which was carried over with the R-134a solvent liquor during the transfer operation. A small volume of the aqueous layer remaining after the extraction was extracted with a roughly equivalent volume of ethyl acetate and the resulting ethyl acetate solution analysed by TLC as before. No cytochalasin D was detected thus confirming that the cytochalasin D was extracted by the R-134a.

What is claimed is:

1. A process for extracting a compound or a composition of matter from a raw material containing the compound or composition or a precursor as a constituent part, the process comprising:
   (1) contacting a sample of the raw material with an extraction solvent comprising 1,1,1,2-tetrafluoroethane and a co-solvent selected from the group consisting of an alkane and a hydrocarbon ether;
   (2) forming a solvent liquor comprising the extraction solvent and an extract from the raw material; and
   (3) separating the solvent liquor containing the extract from the raw material.

2. A process for extracting a compound or composition of matter from a raw material containing the compound or composition as a constituent part, the process comprising the steps of:
   (1) contacting a sample of the raw material with an extraction solvent comprising 1,1,1,2-tetrafluoroethane and a co-solvent selected from the group consisting of an alkane and a hydrocarbon ether;
   (2) forming a solvent liquor comprising the extraction solvent and an extract from the raw material;
   (3) separating the solvent liquor containing the extract from the raw material; and
   (4) recovering the compound or composition of matter.

3. A process for extracting a natural product from a plant material containing the natural product as a constituent part, the process comprising the steps of:
   (1) contacting a sample of the plant material with an extraction solvent comprising 1,1,1,2-tetrafluoroethane and a co-solvent selected from the group consisting of an alkane and a hydrocarbon ether;

(2) forming a solvent liquor comprising the extraction solvent and an extract from the plant material; and (3) separating the solvent liquor containing the extract from the plant material.

4. A process as claimed in any one of claims 1, 2 or 3 wherein the extraction solvent further comprises a (hydro)fluorocarbon having a boiling point of 15° C. or below.

5. A process as claimed in claim 4 wherein the extraction solvent comprises a (hydro)fluorocarbon having a boiling point in the range of from −85 to 15° C.

6. A process as claimed in claim 4 wherein the extraction solvent comprises a (hydro)fluorocarbon having a boiling point of 0° C. or below.

7. A process as claimed in claim 6 wherein the extraction solvent comprises a (hydro)fluorocarbon having a boiling point in the range of from −85 to 0°C.

8. A process as claimed in claim 4 wherein the extraction solvent comprises a (hydro)fluorocarbon having a boiling point of −10° C or below.

9. A process as claimed in claim 8 wherein the extraction solvent comprises a (hydro)fluorocarbon having a boiling point in the range of from −70 to −10° C.

10. A process as claimed in any one of claims 1, 2 or 3 wherein the extraction solvent further comprises a C1–4 hydrofluorocarbon.

11. A process as claimed in claim 10 wherein the extraction solvent further comprises a C1–3 hydrofluorocarbon.

12. A process as claimed in claim 11 wherein the extraction solvent comprises a C1–3 hydrofluorocarbon selected from the group consisting of the hydrofluoromethanes, the hydrofluoroethanes and the hydrofluoropropanes.

13. A process as claimed in any one of claims 1, 2 or 3 wherein the extraction solvent comprises a co-solvent having a boiling point of 20° C. or below.

14. A process as claimed in claim 13 wherein the extraction solvent comprises a co-solvent having a boiling point in the range of from −85 to 20° C.

15. A process as claimed in claim 14 wherein the extraction solvent comprises a co-solvent having a boiling point of 10° C. or below.

16. A process as claimed in claim 15 wherein the extraction solvent comprises a co-solvent having a boiling point in the range of from −70 to 10° C.

17. A process as claimed in claim 13 wherein the extraction solvent comprises a co-solvent having a boiling point of 0° C. or below.

18. A process as claimed in claim 17 wherein the extraction solvent comprises a co-solvent having a boiling point in the range of from −60 to 0° C.

19. A process as claimed in any one of claims 1, 2 or 3 wherein the co-solvent is a C2–6 hydrocarbon.

20. A process as claimed in claim 19 wherein the co-solvent is a C2–4 hydrocarbon.

21. A process as claimed in any one of claims 1, 2 or 3 wherein the co-solvent is a dialkyl ether.

22. A process as claimed in any one of claims 1, 2 or 3 wherein the co-solvent is dimethyl ether, butane or a mixture thereof.

23. A process as claimed in any one of claims 1, 2 or 3 wherein the extraction solvent comprises from 50.0 to 99.5% by weight of the 1,1,1,2-tetrafluoroethane and from 50.0 to 0.5% by weight of the co-solvent.

24. A process as claimed in either of claims 1, 2 or 3, wherein the extract comprises a biologically active substance or a precursor thereof.

25. A process as claimed in either of claims 1, 2 or 3, wherein the extract comprises a pesticide or a precursor thereof.

26. A process as claimed in either of claims 1, 2 or 3, wherein the extract comprises a pharmaceutically active substance or precursor thereof.

27. The process as claimed in claim 26, wherein the extract comprises a penicillin, an alkaloid, paclitaxel, monensin or cytochalasin.

28. The process as claimed in either of claims 1, 2 or 3, wherein the extract comprises a flavored or aromatic oil.

* * * * *